United States Patent [19]

Littlewood et al.

[11] 4,018,789
[45] Apr. 19, 1977

[54] 5-SUBSTITUTED-2-(2')-BENZIMIDAZOYL-FURANS

[75] Inventors: Peter Stuart Littlewood, Menston; Alec Victor Mercer, Bramhope, both of England

[73] Assignee: Sandoz Ltd., Basel, Switzerland

[22] Filed: May 19, 1975

[21] Appl. No.: 578,839

[30] Foreign Application Priority Data

May 23, 1974 United Kingdom ............ 23015/74
Nov. 15, 1974 United Kingdom ............ 49461/74
Dec. 17, 1974 United Kingdom ............ 54386/74

[52] U.S. Cl. .................. 260/309.2; 252/301.27; 252/301.29; 260/240 G; 260/293.6; 260/308 A; 260/310 R; 252/301.25; 252/301.26
[51] Int. Cl.$^2$ ..................................... C07D 405/14
[58] Field of Search .................. 260/309.2, 293.6

[56] References Cited

UNITED STATES PATENTS

| | | | |
|---|---|---|---|
| 3,155,571 | 11/1964 | Sarett et al. .................. | 260/309.2 |
| 3,162,574 | 12/1964 | Forsyth et al. ................ | 260/309.2 |
| 3,174,974 | 3/1965 | Siegrist et al. ................ | 260/309.2 |
| 3,497,525 | 2/1970 | Harnisch et al. .............. | 260/309.2 |
| 3,637,734 | 1/1972 | Harnisch et al. .............. | 260/309.2 |

FOREIGN PATENTS OR APPLICATIONS 1,461,397 11/1966 France

Primary Examiner—Natalie Trousof
Attorney, Agent, or Firm—Gerald D. Sharkin; Richard E. Vila; Thomas C. Doyle

[57] ABSTRACT

Disclosed are optical brightening agents, such agents being 2-(2')-benzimidazoyl-furans substituted in the 5-position of the furan ring by a 1-aryl-pyrazolyl-3, -4 or -5 radical, by a pyrazolyl-1 radical or by a 2-aryl-v-triazolyl-4 radical, such compounds being in free base, acid addition or quaternary ammonium salt form.

30 Claims, No Drawings

5-SUBSTITUTED-2-(2')-BENZIMIDAZOYL-FURANS

The invention relates to furan derivatives.

According to the invention there are provided optical brightening agents, such agents being 2-(2')-benzimidazoyl-furans substituted in the 5-position of the furan ring by a 1-aryl-pyrazolyl-3, -4 or -5 radical, by a pyrazolyl-1 radical or by a 2-aryl-v-triazolyl-4 radical, such compounds being in free base, acid addition or quaternary ammonium salt form.

The compounds provided by the invention may be substituted by a wide variety of substituents, such substituents being chosen so as not deleteriously to affect the brightening activity of the compounds or their application to substrates being brightened, suitable examples being hereinafter given.

Representative of the compounds of the invention are the compounds of formula I,

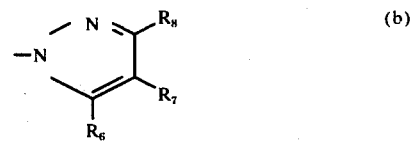

in which
$R_1$ and $R_2$, independently, signify hydrogen, $C_{1-4}$alkyl, $C_{1-4}$ alkoxy, chlorine, fluorine or $C_{1-4}$alkoxy-carbonyl, $R_4$ signifies hydrogen; phenyl; unsubstituted $C_{1-4}$-alkyl or $C_{1-4}$alkyl substituted by a substituent selected from hydroxy, cyano, amino-carbonyl, phenyl, $C_{2-4}$alkenyl, carboxy, $C_{1-4}$alkoxy-carbonyl, $C_{1-4}$alkoxy-($C_{1-4}$)-alkoxy-carbonyl, -CONHR$_{18}$ and -CONR$_{19}$R$_{20}$, $R_{18}$ signifies $C_{1-4}$alkyl, unsubstituted or substituted by a di-($C_{1-4}$)-alkylamino group, either $R_{19}$ and $R_{20}$, independently, have one of the significances of $R_{18}$, or are joined to form, with the nitrogen atom, a 5- or 6-membered, saturated or unsaturated, heterocyclic ring, optionally containing a further heteroatom selected from oxygen and nitrogen and optionally substituted by a $C_{1-4}$alykl group, Y signifies a radical of formula (a), (b) or (c),

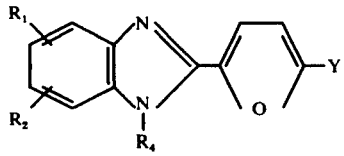

in which either
$R_9$ and $R_{10}$, independently, signify hydrogen, $C_{1-4}$alkyl or phenyl, provided both do not simultaneously signify phenyl, or one of
$R_9$ and $R_{10}$ signifies a 4-bromo- or 4-chloro-substituent, the other being as defined above,
$R_{11}$ and $R_{12}$, independently, signify hydrogen, $C_{1-4}$-alkyl, $C_{1-4}$alkoxy, chlorine, fluorine, cyano, $C_{1-4}$alkoxycarbonyl, -CONR$_{14}$R$_{15}$, -SO$_2$NR$_{14}$R$_{15}$, -SO$_2$R$_{16}$ or -SO$_3$M, with the proviso that $R_{11}$ and $R_{12}$ do not both simultaneously signify groups selected from cyano, $C_{1-4}$alkoxycarbonyl -CONR$_{14}$R$_{15}$ -SO$_2$NR$_{14}$R$_{15}$ and -SO$_2$R$_{16}$, either $R_{14}$ and $R_{15}$, independently, signify hydrogen, unsubstituted $C_{1-8}$alkyl, or $C_{1-4}$alkyl substituted by a substituent selected from hydroxy, cyano and aminocarbonyl, or $R_{14}$ and $R_{15}$, together with the nitrogen atom to which they are attached, signify a five or six membered, saturated or unsaturated, heterocyclic ring which may contain a further hetero atom selected from oxygen and nitrogen and optionally substituted by $C_{1-4}$alkyl, $R_{16}$ signifies $C_{1-4}$alkyl, and M signifies hydrogen or a non-chromophoric cation;

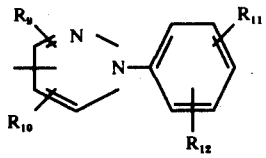

in which either $R_6$, $R_7$ and $R_8$, independently, signify hydrogen or $C_{1-4}$alkyl, or one of $R_6$, $R_7$ and $R_8$, signifies

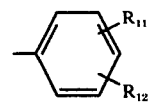

in which $R_{11}$ and $R_{12}$ are as defined above, the other two, independently, signifying hydrogen or $C_{1-4}$alkyl;

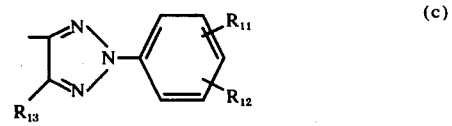

in which $R_{11}$ and $R_{12}$ are as defined above, and $R_{13}$ signifies hydrogen, $C_{1-4}$alkyl, chlorine or bromine, which compounds are in free base, acid addition salt or quaternary ammonium salt form.

In the compounds of formula I, $R_1$ and $R_2$, independently, preferably signify hydrogen, $C_{1-4}$alkyl or $C_{1-4}$alkoxy; more preferably both signify hydrogen.

$R_4$ preferably signifies hydrogen, $C_{1-4}$alkyl, cyanomethyl, β-cyanoethyl, β-hydroxyethyl, benzyl, phenyl, $C_{1-4}$alkoxycarbonyl-$C_{1-4}$alkyl, aminocarbonyl-($C_{1-2}$)alkyl, dimethylamino-($C_{1-2}$)alkyl or carboxy-($C_{1-2}$)alkyl, more preferably, hydrogen, $C_{1-4}$alkyl, β-cyanoethyl, phenyl or $C_{1-4}$alkoxycarbonyl-($C_{1-4}$)alkyl, most preferably hydrogen, methyl or $C_{1-4}$alkoxycarbonyl-($C_{1-4}$)alkyl, of which latter radicals methoxy- and ethoxycarbonylmethyl are particularly preferred.

$R_9$ and $R_{10}$, independently, preferably signify hydrogen or $C_{1-4}$alkyl, or one of $R_9$ and $R_{10}$ signifies a 4-chloro-substituent, the other hydrogen or $C_{1-4}$alkyl. Most preferably $R_9$ and $R_{10}$ both signify hydrogen.

$R_{11}$ preferably signifies hydrogen, $C_{1-4}$alkyl, $C_{1-4}$alkoxy, chlorine, cyano, $C_{1-4}$alkoxy-carbonyl, -SO$_2$R$_{16}$, -CONR$_{14}$'R$_{15}$', -SO$_2$NR$_{14}$'R$_{15}$' or -SO$_3$M, where $R_{14}$' and $R_{15}$', independently, signify hydrogen or $C_{1-}$ ₄alkyl or, together with the nitrogen atom, signify a five or six membered saturated or unsaturated heterocyclic ring which may contain a further hetero atom selected from O and N, optionally substituted by methyl. Any heterocyclic ring as -NR$_{14}$R$_{15}$, -NR$_{14}'$R$_{15}'$ or -NR$_{19}$R$_{20}$ is preferably a morpholino, piperidino or N-methylpiperazino ring. M preferably signifies hydrogen, an alkali or a alkaline earth metal cation or a cation of formula R$_{21}$R$_{22}$R$_{23}$-NH$^+$ in which R$_{21}$, R$_{22}$ and R$_{23}$, independently, signify hydrogen or C$_{1-4}$alkyl, unsubstituted or substituted by up to two, preferably one, hydroxy group. As examples of M may be given the lithium, sodium, potassium, calcium, magnesium, ammonium, mono-, di- and tri-ethanolammonium and tri-isopropanolammonium cations. The preferred cations are the alkali metal cations, particularly sodium.

More preferably R$_{11}$ signifies hydrogen, C$_{1-4}$-alkyl, C$_{1-4}$alkoxy, chloro, cyano, -CONH$_2$, -SO$_2$NH$_2$ or -SO$_2$CH$_3$.

Most preferably R$_{11}$ signifies hydrogen or chloro.

R$_{12}$ preferably signifies hydrogen.

R$_{13}$ preferably signifies hydrogen or C$_{1-4}$alkyl.

The preferred significances of Y are the radicals of formula (b) as defined above, the radicals of formula (a'),

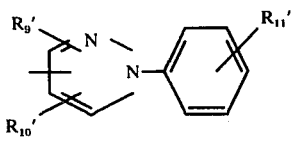

in which

R$_9'$ and R$_{10}'$, independently, signify hydrogen or C$_{1-4}$alkyl, and

R$_{11}'$ signifies hydrogen, C$_{1-4}$alkyl, C$_{1-4}$alkoxy, chlorine, cyano, C$_{1-4}$-alkoxycarbonyl, -CONR$_{14}'$R$_{15}'$, -SONR$_{14}'$R$_{15}'$, -SO$_2$R$_{16}$ or -SO$_3$M, in which R$_{14}'$, R$_{15}'$, R$_{16}$ and M are as defined above;

and the radicals of formula (c')

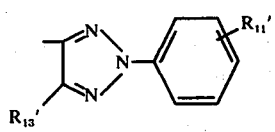

in which R$_{11}'$ is as defined above, and

R$_{13}'$ signifies hydrogen or C$_{1-4}$alkyl.

Where Y signifies a radical of formula (a) or (a'), such is preferably a pyrazolyl 3- or -5 radical, more preferably a pyrazolyl radical.

Further preferred significances of Y are radicals of formulae (a'') and (c''),

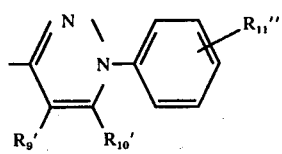

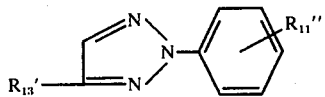

where

R$_9'$, R$_{10}'$ and R$_{13}'$ are as defined above, and

R$_{11}''$ signifies hydrogen, C$_{1-4}$alkyl, C$_{1-4}$alkoxy, chloro, cyano, -CONH$_2$, -SO$_2$NH$_2$ or -SO$_2$CH$_3$ The most preferred significances of Y are the radicals of formula (a''), particularly those in which R$_9'$ and R$_{10}'$ both signify hydrogen and R$_{11}''$ signifies hydrogen or chlorine, which chlorine is preferably in para-position.

As a preferred group of compounds of formula I, may be given the compounds of formula I',

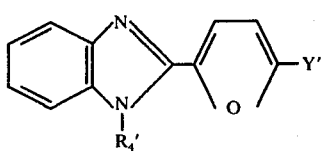

in which

R$_4'$ signifies hydrogen, C$_{1-4}$alkyl, or C$_{1-4}$alkyl substituted by a C$_{1-4}$alkoxycarbonyl group, preferably hydrogen, methyl, ethoxycarbonyl-methyl or methoxycarbonylmethyl, more preferably methyl or methoxycarbonylmethyl or ethoxycarbonylmethyl, Y' signifies a radical of formula (a'), (b) or (c'), as defined above, preferably of formula (a'') or (c''), more preferably of formula (a''), most preferably of formula (a'') in which R$_9'$ and R$_{10}'$ are both hydrogen and R$_{11}''$ is hydrogen or chlorine, any chlorine as R$_{11}''$ preferably being in the p-position, which compounds are in free base, acid addition salt or quaternary ammonium salt form.

As regards the acid addition and quaternary ammonium salt forms of the compounds of the invention, such arise from the basic nature of the nitrogen atoms in the benzimidazole and pyrazole and triazole rings, the nitrogen atoms in the latter two rings being less basic than in the benzimidazole ring but being capable of forming acid addition and quaternary ammonium salt forms under forcing conditions. Any acid addition salt or quaternary ammonium salt, however, preferably results from protonation or quaternisation solely of the benzimidazole nitrogen, i.e. by avoiding the forcing conditions likely to yield protonation or quaternisation of the pyrazole or triazole ring. Further, where the compounds contain a dialkylamino substituent, such substituent will, of course, be protonisable and quaternisable. Indeed, the basicity thereof is generally higher than that of the nitrogen atoms in the benzimidazole ring and, accordingly, quaternisation and protonisation will tend to occur there first. In such a situation, the quaternisation conditions are preferably such that only the dialkylamino group is quaternised or protonised since, of the quaternised and protonised compounds, those quaternised or protonised at a single site are preferred. The anions in the acid addition salt and quaternary ammonium salt forms may suitably be any anions conventional in the optical brightener art, the exact nature thereof not being critical, provided such anions are non-chromophoric. As examples of suitable anions may be given carboxylic acid anions, e.g. the formate, acetate, propionate and oxalate ions, alkyl sulphate ions, e.g. methyl, ethyl and propyl sulphate ions, inorganic acid anions, e.g. chloride bromide, sulphate, bisulphate, iodide, fluoroborate and perchlorate anions, sulphonic acid anions, e.g. p-toluene-and benzene-sulphonate anions and complex anions, e.g. the chlorozincate anion. The preferred anions are the methylsulphate, ethylsulphate, chloride, sulphate, chlorozincate, formate, acetate and p-toluenesulphonate anions. As examples of suitable quaternating groups may be given benzyl, $C_{1-4}$-alkyl, unsubstituted or substituted by a $C_{1-4}$alkoxycarbonyl, carboxyl, $C_{1-4}$alkoxy-($C_{1-4}$)alkoxycarbonyl, $C_{2-4}$alkenyl (e.g. -CH=CH$_2$, CH$_3$CH=CH- and -CH$_2$=C(CH$_3$) ), nitrile, amino-carbonyl or by a mono- or di-$C_{1-4}$alkylaminocarbonyl radical; benzyl, $C_{1-4}$alkyl (particularly methyl) and $C_{1-4}$alkoxycarbonyl-$C_{1-4}$alkyl (particularly methoxy- and ethoxycarbonyl-methyl) being preferred.

In the compounds of formulae I and I', any alkyl radical or moiety, unless otherwise stated, is preferably methyl.

The compounds of the invention may, for example, be produced by reacting an o-phenylenediamine with a 2-formylfuran substituted in the 5-position by a 1-aryl-pyrazolyl-3,-4 or -5 radical, by a pyrazolyl-1 radical or by a 2-aryl-v-triazolyl-4 radical.

The invention also provides a process for the production of compounds of formula I, characterised by ai.
reacting a compound of formula II,

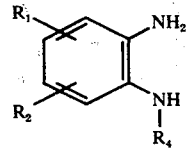

II in which $R_1$, $R_2$ and $R_4$ are as defined above, with a compound of formula III

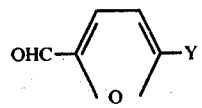

III in which Y is as defined above, in the presence of an alkali-metal metabisulphite, aii. oxidising a compound of formula IV,

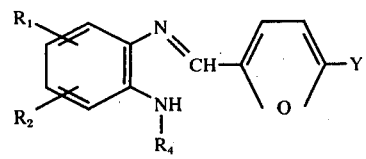

IV in which $R_1$, $R_2$, $R_4$ and Y are as defined above,
aiii. reacting a compound of formula II, defined above, with a compound of formula V,

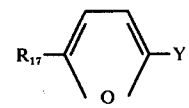

V in which Y is as defined above, and
$R_{17}$ signifies cyano or -CORx, where Rx is hydroxy, $C_{1-4}$alkoxy, amino, mono-($C_{1-4}$)alkylamino, di-($C_{1-4}$)-alkylamino or chlorine b. obtaining a compound of formula I, in which Y signifies a radical of formula (a) or (b), with the proviso that $R_9$ and $R_{10}$ both signify other than a 4-chloro- or 4-bromo-substituent, by oxidising a compound of formula VI,

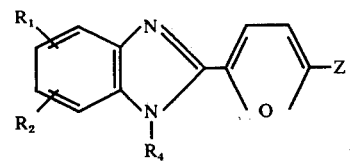

VI where $R_1$, $R_2$ and $R_4$ are as defined above, and Z signifies a radical of formula (d), (e), (f) or (g),

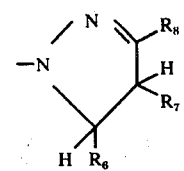

(d)

in which $R_6$, $R_7$ and $R_8$ are as defined above,

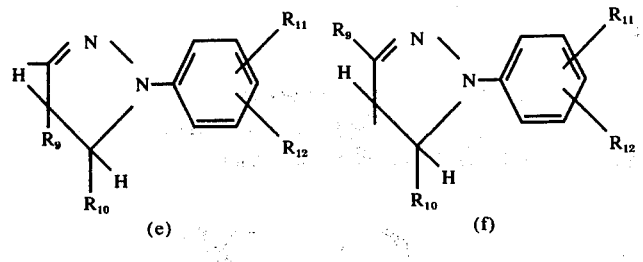

in which $R_9$, $R_{10}$, $R_{11}$ and $R_{12}$ are as defined above, with the proviso that $R_9$ and $R_{10}$ each signify other than a 4-chloro- or 4-bromo-substituent.

c. obtaining a compound of formula I, in which Y signifies a radical of formula (a), with the proviso that $R_9$ and $R_{10}$ both signify other than a 4-chloro- or 4-bromo-substituent, by reacting a compound of formula VII,

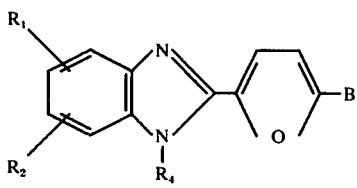

in which $R_1$, $R_2$ and $R_4$ are as defined above, and B signifies a radical of formula (h) or (i),

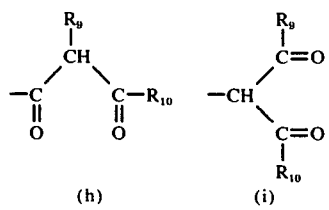

in which $R_9$ and $R_{10}$ are as defined above, with the proviso that neither signifies a chlorine or bromine atom, with a hydrazine of formula VIII,

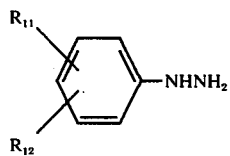

in which $R_{11}$ and $R_{12}$ are as defined above, b. obtaining a compound of formula I, in which Y signifies a radical of formula (b), by reacting a compound of formula IX,

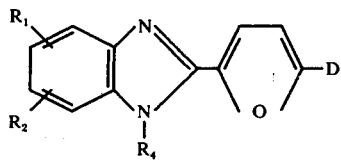

in which $R_1$, $R_2$ and $R_4$ are as defined above, and D signifies chlorine, bromine, iodine or $C_{1-4}$alkylsulphonyl, with a compound of formula X,

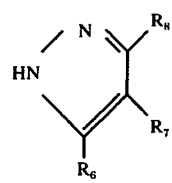

in which $R_6$, $R_7$ and $R_8$ are as defined above,
  e. obtaining a compound of formula I, in which Y signifies a radical of formula (c), by
    ei. cyclising a compound of formula XI,

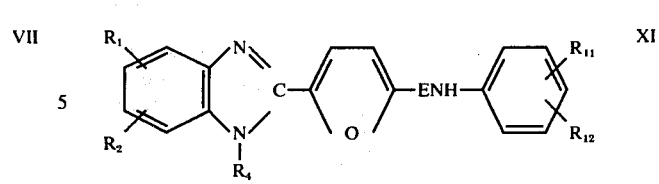

where
  $R_1$, $R_2$, $R_4$, $R_{11}$ and $R_{12}$ are as defined above,
  E signifies a radical of formula (j) or (k),

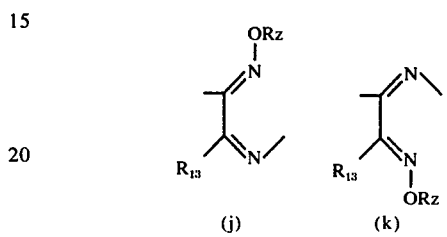

in which
  $R_{13}$ is as defined above, and
  Rz signifies hydrogen or an acyl radical, or
  eii. reducing an N-oxide of formula XII

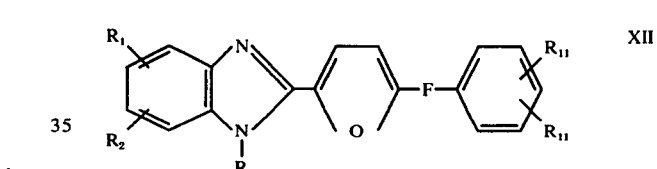

in which $R_1$, $R_2$, $R_4$, $R_{11}$ and $R_{12}$ are as defined above, and F signifies a radical of formula (l) or (m),

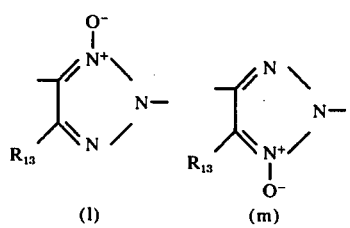

in which $R_{13}$ is as defined above,
  f. obtaining a compound of formula I, in which Y signifies a radical of formula (aa),

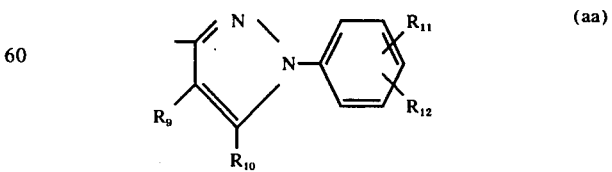

in which $R_9$, $R_{10}$, $R_{11}$ and $R_{12}$ are as defined above, by reacting a compound of formula XIII,

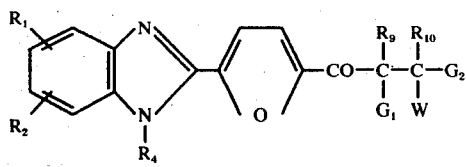

in which $R_1$, $R_2$, $R_4$, $R_9$ and $R_{10}$ are as defined above, and one of $G_1$ and $G_2$ signifies hydrogen, the other halogen, $C_{1-4}$alkoxy, di-$(C_{1-4})$alkylamino or diarylamino, e.g. diphenylamino, and W signifies halogen, $C_{1-4}$alkoxy, di-$(C_{1-4})$alkylamino or diarylamino, e.g. diphenylamino, with a compound of formula VIII, defined above, g. obtaining a compound of formula I, in which Y signifies a radical of formula (aa), defined above, in which $R_9$ signifies hydrogen, by reacting a compound of formula XIV,

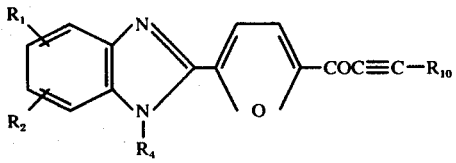

in which $R_1$, $R_2$, $R_4$ and $R_{10}$ are as defined above, with a compound of formula VIII, as defined above, h. obtaining a compound of formula I, in which Y signifies a radical of formula (a), in which one of $R_9$ or $R_{10}$ signifies a 4-bromo- or 4-chloro-substituent, by chlorinating or brominating a compound of formula I, in free base form, and in which Y signifies a radical of formula (a), in which the 4-position of the pyrazole ring is unsubstituted, and, where required, converting the free base form of a compound of formula I, as obtained by any of the above processes a) to h), into acid addition or quaternary ammonium salt form.

The processes may be carried out in conventional manner for the respective types of reaction involved.

The reaction of the o-phenylenediamines with the 2-formylfurans, in particular process ai), is conveniently carried out in an aqueous polar solvent, such as in aqueous methanol, ethanol or isopropanol, aqueous cellosolve or aqueous dimethylformamide. A suitable reaction temperature is from 20° to 150° C, preferably from 70° to 150° C. It is preferred to use at least one equivalent of the alkali-metal metabisulphite, more preferably from 2 to 3 equivalents thereof. The preferred metabisulphite is sodium metabisulphite.

In process aii), suitable oxidising agents are air, manganese dioxide, lead tetra-acetate and sodium hypochlorite. The reaction is suitably carried out in an inert solvent, such as in ethanol, aqueous ethanol, acetone, glacial acetic acid, dimethylformamide, xylene, chlorobenzene, carbon tetrachloride or pyridine. A suitable reaction temperature is from 0° to 200° C, preferably from 20° to 200° C.

Process aiii) may be carried out in the presence or absence of a solvent. Where a solvent is employed, suitable solvents include o-dichlorobenzene, sulpholane, xylene and dimethylformamide. The reaction is preferably carried out in the presence of a catalyst such as boric acid, zinc chloride, polyphosphoric acid or p-toluene sulphonic acid. A suitable reaction temperature is from 90° to 260° C, preferably from 130° to 240° C.

Process b) may be carried out in the presence or absence or solvent, preferably, however, in a solvent. Suitable solvents include toluene, chlorobenzene, trichloroethylene, ethanol, cellosolve, dimethylformamide, sulpholane, glacial acetic acid and sulphuric acid. Suitable oxidising agents include sulphur, chlorine, chromium trixoide, sodium dichromate, potassium permanganate, nitric acid, manganese dioxide, potassium ferricyanide, sodium chlorite and palladium on charcoal. A suitable reaction temperature is from 0° to 300° C, preferably from 20° to 200° C.

Process c) is conveniently carried out in an inert solvent. Suitable solvents include water, glacial acetic acid, methanol, cellosolve, dimethylformamide, toluene and o-dichlorobenzene. A suitable reaction temperature is from 0° to 150° C, preferably from 20° to 100° C.

Where, in the compound of formula VII, B signifies a radical of formula (h), a two isomer mixture is obtained, one where Y is a radical of formula (aa), as defined above, the other where Y is a radical of formula (ab),

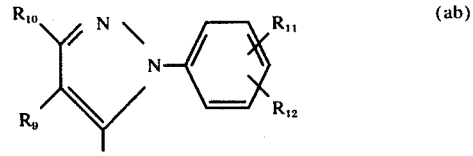

in which $R_9$, $R_{10}$, $R_{11}$ and $R_{12}$ are as defined above, with the proviso that $R_9$ signifies other than a chlorine or bromine atom.

Such mixture may be separated into the respective isomers in conventional manner. However, the isomer mixture need not be separated but camn be used as such, as hereinafter described.

Where, in the compound of formula VII, B signifies a radical of formula (i), a compound of formula I is obtained wherein Y signifies a group of formula (ac),

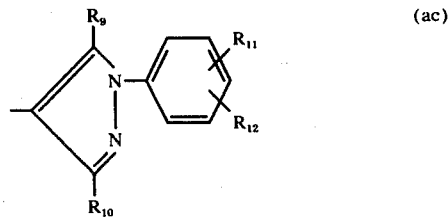

in which $R_9$, $R_{10}$, $R_{11}$ and $R_{12}$ are as defined above.

Process d) may be carried out in the presence or absence of a solvent, preferably in the presence of a solvent. Suitable solvents include pyridine, dimethylformamide, sulpholane, o-dichlorobenzene and nitrobenzene. The reaction is preferably carried out in the presence of a copper compound, such as copper (II) oxide, cuprous bromide or cuprous chloride and in the presence of an acid acceptor, e.g. potassium carbonate, magnesium oxide or calcium oxide. A suitable reaction temperature is from 80° to 250° C, preferably from 100° to 200° C. Where, in the compound of formula X, $R_6$ and $R_8$ are different, a mixture of two isomers may be obtained. Where this occurs, the mixture may be used, as hereinafter described, or, if desired, the isomers may be separated using conventional techniques.

Process ei) may be carried out by simple pyrolysis of the compound of formula XI by subjection to temperatures in excess of 200° C. Alternatively, the reaction can be carried out in a solvent, such as in phosphoric acid tris-dimethylamide, sulpholane or dimethylformamide at a temperature of from 20° C to 150° C, preferably, where Rz signifies hydrogen, in the presence of a dehydrating agent such as acetic anhydride, phosgene or acetyl chloride. Further, the reaction can be carried out in molten urea at a temperature of from 140° to 200° C, preferably 150° to 180° C.

Process eii) is conveniently carried out in an inert solvent, such as in water, aromatic hydrocarbons or dimethylformamide, preferably in an organic acid such as formic acid, acetic acid or aqueous acetic acid. Suitable reducing agents are salts of tin (II) compounds, ferrous salts and iron and zinc powders. A suitable reaction temperature is from 20° to 150° C, preferably from 80° to 120° C. Those compounds of formula XII, in which $R_{13}$ signifies hydrogen, can alternatively be reduced to compounds of formula I, in which $R_{13}$ signifies chlorine or bromine by treatment with hydrogen chloride or hydrogen bromide, respectively. Such reaction is conveniently carried out in an inert solvent, such as in aqueous or non-aqueous ethylene glycol or dioxan, or in aqueous diethyleneglycoldimethylether. A suitable temperature for such reaction is from 70° to 250° C, preferably from 70° to 150° C.

Process f) is conveniently carried out in a solvent. Suitable solvents include glacial acetic acid, isopropanol, cellosolve and dimethylformamide, optionally in the presence of water. A suitable reaction temperature is from 0° to 150° C, preferably from 20° to 150° C.

Process g) is conveniently carried out in a solvent. Suitable solvents include glacial acetic acid, methanol, cellosolve, dimethylformamide, toluene, chlorobenzene and trichloroethylene. A suitable reaction temperature is from 0° to 200° C, preferably from 20° to 150° C.

Process h) is conveniently carried out in an inert solvent, such as in water, carbon tetrachloride or concentrated hydrochloric acid. Suitable halogenating agents include chlorine, bromine and sulphuryl chloride. The halogenating agent may be generated in situ, for example by adding an aqueous solution of an alkali-metal chlorate to a solution or suspension of the pyrazole in concentrated hydrochloric acid. A suitable reaction temperature is from 0° C to 100° C, preferably from 20° to 80° C.

The formation of the acid addition or quaternary ammonium salt forms may be carried out in conventional manner, conveniently in a solvent. Preferably at least one equivalent of the protonating or quaternating agent is employed. Where it is desired to obtain a compound of formula I, quaternised with an alkyl radical, preferred alkylating agents include dialkyl sulphates, such as dimethyl and diethyl sulphates, alkyl halides, such as methyl iodide, ethyl iodide, propyl iodide and butyl bromide and alkyl toluene sulphonates, such as methyl-p-toluenesulphonate. Where it is desired to obtain a compound of formula I, quaternised by a benzyl radical, preferred benzylating agents are the benzyl halides, such as benzyl chloride. As examples of other quaternising agents may be given the compounds $ClCH_2CO_2CH_2CH_3$, $BrCH_2-CH=CH_2$, $BrCH_2COOH$, $ClCH_2CONHCH_3$ and $ClCH_2CON(CH_3)_2$. Where it is desired to obtain a protonated compound of formula I, i.e. in acid addition salt form, suitable protonating agents include mineral and organic acids. As will be appreciated, preferred quaternising and protonating agents are those which yield the preferred anions, as set out above. However, interconversion of salt forms by interchanging anions may be carried out in conventional manner. Suitable solvents for use in the quaternisation or protonation reaction include tri-chloroethylene, toluene, chlorobenzene, dioxan, dimethylformamide, methanol, ethanol, and water. Where the process is carried out on compounds in which $R_4$ is hydrogen, the reaction is preferably carried out in the presence of an inorganic base such as potassium, sodium or calcium carbonate or sodium, potassium or magnesium hydroxide, or in the presence of an organic base such as tri-ethylamine or benzyl tri-methylammonium hydroxide. A suitable reaction temperature is from 0° to 150° C, preferably from 20° to 100° C.

Where a sulphonyl or carboxyl group is contained in the compounds undergoing quaternisation, such group would generally be esterified by the quaternating agent but can readily be hydrolysed back to the free acid form.

The resulting compounds of formula I may be isolated and purified using conventional techniques.

As will be appreciated, the compounds of formula I can be interconverted, for example, compounds of formula I, in free base form and in which $R_4$ is hydrogen, may readily be converted into compounds of formula I, where $R_4$ is other than hydrogen, by alkylation etc. Such interconversion may be carried out in conventional manner, e.g. using appropriate alkylating agents. Where it is desired to obtain a compound of formula I, in which $R_4$ is hydroxy-alkyl, suitable reagents include alkylene oxides, such as ethylene and propylene oxide and where it is desired to obtain a compound of formula I in which $R_4$ is cyano-alkyl or aminocarbonylalkyl, such reagents as acrylonitrile and acrylamide may be used. Where it is desired to obtain a compound of formula I in which $R_4$ signifies phenyl, suitable reagents include bromobenzene and iodobenzene. Suitable solvents for such interconversions include chloroform, trichloroethylene, benzene, toluene, chlorobenzene, dioxan, dimethylformamide, methanol, ethanol, isopropanol, cellosolve and water. The reaction is preferably carried out in the presence of a base, e.g. an inorganic base such as potassium carbonate, sodium carbonate, sodium hydroxide, potassium hydroxide, calcium hydroxide, magnesium oxide, or an organic base such as triethylamine or benzyltrimethylammonium hydroxide. Where compounds of formula I are being obtained in which $R_4$ signifies phenyl, the reaction is advantageously carried out in the presence of a catalytic amount of a cuprous salt, for example of cuprous bromide. A suitable reaction temperature is from 0° C to 200° C, preferably 0° C to 150° C.

The compounds of formulae II, III, IV, V, VI, VII, VIII, IX, X, XI, XIII and XIV are either known or may be obtained from available starting materials in conventional manner.

The compounds of formula VI, in which Z is a radical of formula (e), i.e. compounds of formula VIe,

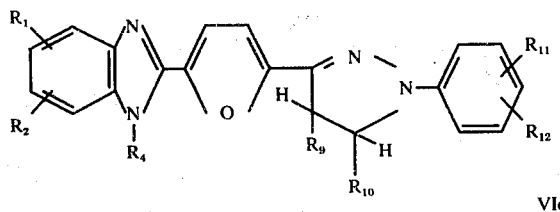

Vle in which $R_1$, $R_2$, $R_4$, $R_9$, $R_{10}$, $R_{11}$ and $R_{12}$ are as defined above, with the proviso that $R_9$ is other than chlorine or bromine, are new and are particularly valuable intermediates for the production of the corresponding compounds of formula I. They form a further aspect of the invention and may be obtained by reacting a compound of formula XIV,

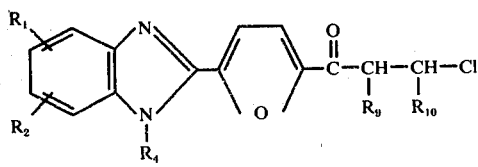

XIV in which $R_1$, $R_2$, $R_4$, $R_9$ and $R_{10}$ are as defined above, with a compound of formula VIII, stated above.

Such reaction may be carried out in conventional manner, e.g. in an inert solvent, such as in lower $(C_{1-4})$-alcohols, dimethylformamide, acetic acid, water, benzene or chlorobenzene. A suitable reaction temperature is from 0° to 150° C, preferably from 20° to 100° C. A wide pH range may be employed, e.g. from a value of 1 to 12, preferably from 2 to 10. Isolation and purification of the resulting compounds of formula VIe may be carried out in conventional manner.

The compounds of formula XIV may be obtained in conventional manner from available starting materials.

The compounds of formula XII may conveniently be obtained by oxidative cyclisation of compounds of formula XI, above, in which Rz signifies hydrogen.

This oxidation cyclisation is suitably carried out under alkaline conditions and in a solvent, such as in aqueous pyridine, aqueous picoline and aqueous alkyl pyridines. Alternatively, it may be carried out under aqueous acidic conditions such as in aqueous sulphuric or aqueous acetic acid. As examples of suitable oxidising agents may be given cupric sulphate, potassium ferricyanide, sodium dichromate and sodium hypochlorite. As a further alternative, the reaction can be carried out in chloroform or glacial acetic acid, using lead tetra-acetate as oxidising agent. A suitable reaction temperature for the oxidative cyclisation is from 0° to 150° C, preferably from 0° to 120° C.

The compounds of the invention and mixtures thereof, particularly isomer mixtures, obtained as described above, are useful as optical brightening agents.

The compounds of the invention and mixtures thereof are particularly effective optical brightening agents for substrates comprising or consisting of polyacrylonitrile or polyamides. Such substrates may be textile substrates and in fibre, filament, yarn, thread, woven, non-woven, knitted, carpet or piece good form.

The compounds of formula I and mixtures thereof may be applied to polyacrylonitrile-containing substrates in conventional manner. For example, the compounds may be applied by conventional exhaust procedures in which the polyacrilonitrile fabric is introduced, at 40° C, to a bath containing, for example, from 0.001% to 1.0%, preferably 0.05% to 0.5%, of brightener and 1.0% to 5.0%, preferably 2.0% to 4.0% of acetic acid, based on the weight of the substrate. A suitable liquor to goods ratio is from 5:1 to 100:1, preferably from 15:1 to 50:1. The bath is then heated to 90° to 95° C, during 15 to 60, preferably 20 to 40, minutes and maintained at this temperature for 15 to 120, preferably 30 to 60 minutes. The substrate is then removed and rinsed, preferably in warm water, then in cold water, and then dried.

The compounds of the invention can be used to brighten polyamide-containing substrates in conventional manner. A preferred method of application is the so-called "thermosol" procedure described in "Cotton and Man-Made Fibres Year Book", 1966–67, p. 410.

For application to polyamide substrates, the preferred compounds of the invention are those containing a $-SO_3M$ group. For application to polyacrilonitrile substrates, the preferred compounds of the invention are those free from any $-SO_3M$ group. The brightening of polyacrylonitrile substrates is the preferred application of the compounds.

The invention is illustrated by the following Examples, in which all parts and percentages are by weight and all temperatures in degrees centigrade.

EXAMPLE 1 [process d)]

2-(2')-(1-methylbenzimidazoyl)-5-bromofuran (5.54 g), 3,5-dimethylpyrazole (2.5g), cuprous bromide (0.2 g) and potassium carbonate (2.6 g) were stirred together in dimethylsulphoxide (15 ml) and the mixture was heated to the boil. The mixture was stirred under reflux for one hour and then cooled to 20° and poured onto water (100 ml). The precipitated oil was extracted with three 20 ml portions of boiling petroleum ether (b.p. 100°–120°), and the extracts evaporated, to give an oily solid which crystallised from aqueous acetone to give the pyrazole of formula

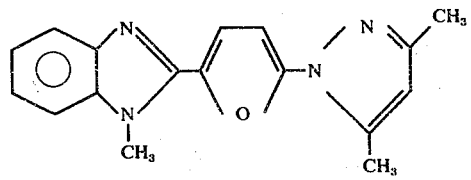

as a white solid.

EXAMPLE 2 [process b)]

2-(2')-(1-methylbenzimidazoyl)-5-(3')-(1-phenylpyrazolinyl)-furan (23.3 g) was stirred with manganese dioxide (8.7 g) in glacial acetic acid (200 ml). The mixture was heated to the boil and concentrated hydrochloric acid (36 % w/w, d = 1.18, 15 ml) was added dropwise to the refluxing mixture over 15 minutes. The mixture was boiled for a further 1 hour, filtered hot to remove excess manganese dioxide and then cooled to 20°. The mixture was then treated with 30% sodium hydroxide solution to give a pH of 4-5 and the solid product filtered, washed well with water and dried to give the pyrazole of formula

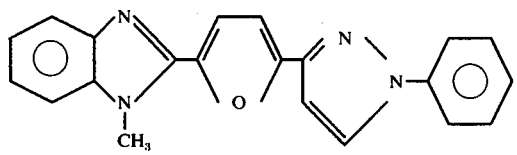

as a white solid.

The 2-(2')-1-methylbenzinidazoyl)-5-(3')-(1-phenyl-pyrazolinyl)-furan, employed as starting material, is obtained by reaction of equimolar quantities of 2-(2')-(1-methylbenzimidazoyl)-5-(2-chloroethylcarbonyl)-furan and phenylhydrazine in dimethylformamide at 90° C over 4 hours in the presence of one molar quantity of sodium carbonate.

The pyrazoles shown in the table are prepared in a similar way to the pyrazole of Example 2, and are of formula

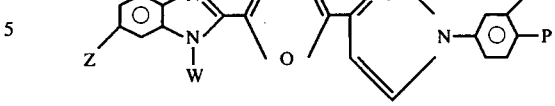

| Example | Z | X | P | W | Appearance |
|---|---|---|---|---|---|
| 3 | H | H | —Cl | CH$_3$ | white solid |
| 4 | H | H | —OCH$_3$ | CH$_3$ | " |
| 5 | H | H | —SO$_2$NH$_2$ | CH$_3$ | " |
| 6 | H | Cl | H | CH$_3$ | " |
| 7 | H | Cl | Cl | CH$_3$ | " |
| 7a | H | H | CH$_3$ | CH$_3$ | " |
| 7b | Cl | H | H | H | " |
| 7c | H | H | H | —CH$_2$CH$_2$CN | " |
| 7d | H | H | H | H | " |
| 7e | H | H | —SO$_3$Na | CH$_3$ | " |
| 7f | CH$_3$ | H | CH$_3$ | CH$_3$ | " |
| 7g | OCH$_3$ | H | CN | CH$_3$ | " |
| 7h | H | H | CONH$_2$ | CH$_3$ | " |
| 7i | F | H | SO$_2$CH$_3$ | CH$_3$ | " |
| 7j | H | H | COOCH$_3$ | CH$_3$ | " |
| 7k | H | H | CON(CH$_2$CH$_2$)$_2$O | CH$_3$ | " |
| 7l | H | H | SO$_2$N(CH$_2$CH$_2$)$_2$N—CH$_3$ | CH$_3$ | " |

Following the procedure of Example 2, above, using appropriate starting materials, the compounds of the following table are prepared, which are of formula

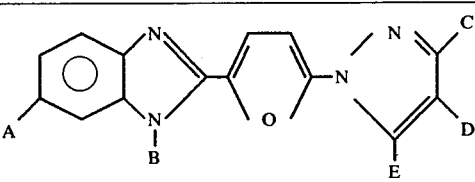

| Example No. | A | B | C | D | E | Appearance |
|---|---|---|---|---|---|---|
| 7m | CH$_3$ | CH$_3$ | CH$_3$ | H | —C$_6$H$_4$—Cl | white solid |
| 7n | OCH$_3$ | H | H | H | —C$_6$H$_4$—CH$_3$ | " |
| 7o | H | CH$_3$ | H | H | —C$_6$H$_4$—OCH$_3$ | " |
| 7p | H | CH$_3$ | —C$_6$H$_4$—SO$_2$CH$_3$ | H | H | " |

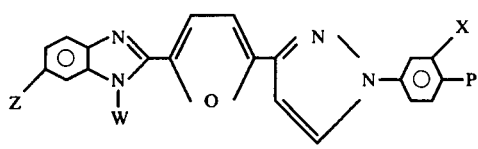

EXAMPLE 8 [process ai)]

2-(5')-(1-phenyl-3-methylpyrazolyl)-5-formyl furan (19.6 g) was dissolved in 2-ethoxyethanol (100 ml) and a solution of sodium metabisulphite (15 g) in water (25 ml) added. The mixture was warmed to 100° and o-phenylenediamine (10.5 g) dissolved in 2-ethoxy ethanol (25 ml) added in one portion. The mixture was stirred and heated to the boil and stirred under reflux for two hours. The mixture was then cooled to 0° and stirred for one hour and the solid filtered off, washed with water and dried to give the pyrazole of formula

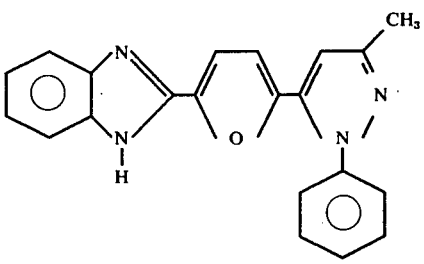

as a white solid.

EXAMPLE 9 (interconversion process)

The pyrazole described in Example 8 (16 g) was dissolved in methanol (250 ml) containing potassium hydroxide (2.7 g). The solution was stirred at 25° as dimethylsulphate (6.5 g) was added dropwise. The temperature of the mixture rose from 25° to 30°. When the temperature of the reaction mixture started to fall, the mixture was warmed to 40° and kept at 40° for 30 minutes. The reaction mixture was then cooled to 20° and water (200 ml) added. The precipitated oily solid was filtered and crystallised from acetone to give the pyrazole of formula

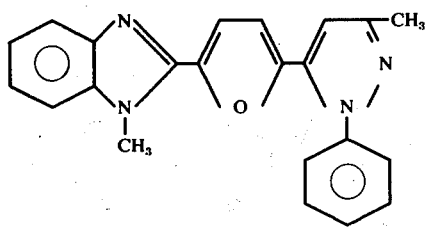

as a white solid.

EXAMPLE 10 [process ai)]

2-(4')-(2-phenyl-5-methyl-v-triazolyl)-5-formyl furan (5.1 g) was dissolved in 2-ethoxyethanol (25 ml) and a solution of sodium metabisulphite (5 g) in water (6.5 ml) added. The mixture was warmed to 100° and o-phenylene diamine (2.73 g) added. The mixture was stirred and heated under reflux for seventeen hours, then cooled to 20° and filtered. The solid was washed with water and dried to give the triazole of formula

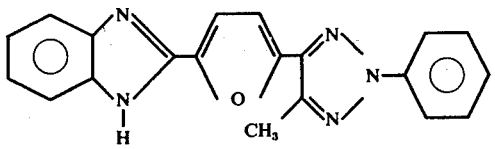

as a white solid.

EXAMPLE 11 [quaternisation]

The pyrazole described in Example 2 (10.0 g) was stirred in dioxan (100 ml) and the mixture heated to the boil. Dimethylsulphate (3.89 g) was added dropwise to the refluxing mixture over 30 minutes and the resulting mixture stirred under reflux for a further 1 hour, and then cooled to 20°. The solid was filtered off and washed with acetone and then dried at 80° to give the quaternary salt of formula

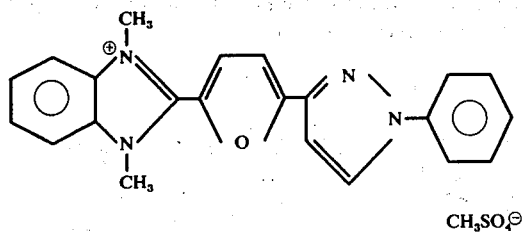

as a pale yellow solid.

Corresponding quaternary salts of the compounds of Examples 3, 4, 5, 6, 7, 7a, 7b, 7c, 9 and 13 were obtained in analogous manner to the procedure employed in Example 11. All such salts were obtained as pale yellow solids.

EXAMPLE 12 [interconversion and quaternisation]

The triazole described in Example 10 (65 g) was mixed with potassium carbonate (1.1 g) in dioxan (50 ml) and dimethylsulphate (3.8 g) added. The mixture was stirred and heated to the boil, and then stirred under reflux for 3 hours. The mixture was cooled to 20° and filtered. The solid was slurried in boiling water (75 ml) and filtered hot and the clear solution cooled to 20°. The precipitated solid was filtered, washed with a little water and dried to give the quaternary salt of the formula

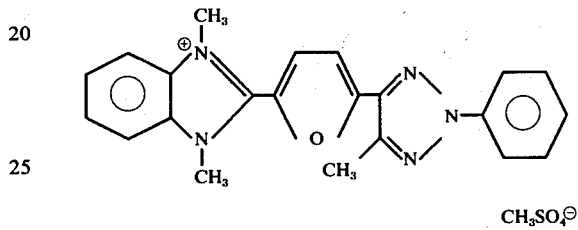

as a pale yellow solid.

EXAMPLE 13 [process b)]

2-(2')-(1-phenylbenzimidazoyl)-5-(3')-(1-p-chlorophenyl pyrazolinyl)-furan (19.0g) was stirred with manganese dioxide (6.6g) in glacial acetic acid (150 ml). The mixture was heated to the boil and concentrated hydrochloric acid (36% W/W, d=1.18, 12 ml) was added dropwise to the refluxing mixture over 15 minutes. The mixture was boiled for a further 1 hour, filtered hot to remove excess manganese dioxide and the solution evaporated to give a pale yellow solid. The solid was slurried in water (200 ml) and the pH of the slurry adjusted to 7–8 with 30% W/W sodium hydroxide solution. The solid was filtered, washed well with water and crystallised from 2-ethoxyethanol to give the pyrazole of formula

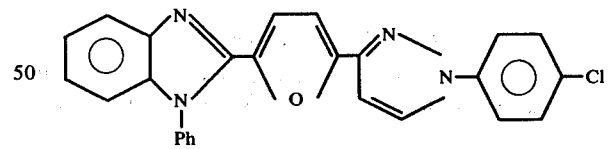

as a white solid.

EXAMPLE 14 [process h)]

The pyrazole described in Example 2 (3.4g) was dissolved in concentrated hydrochloric acid (36 W/W, d=1.18, 100 ml) and the solution stirred as a solution of sodium chlorate (0.4g) in water (4 ml) was added dropwise, keeping the temperature below 35°. The mixture was stirred for 30 minutes after the addition of sodium chlorate and poured onto ice (50g). The suspension was adjusted to pH 4–5 by addition of 35% W/W sodium hydroxide solution and the solid filtered and washed well with water and dried at 80° to give the pyrazole of formula

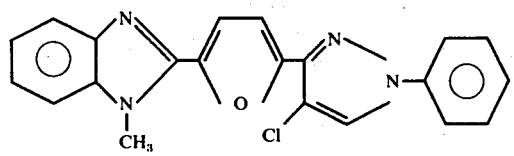

as a white solid.

EXAMPLE 15 [process b)]

Following the procedure of Example 2 and using appropriate starting materials, the following compounds are prepared.

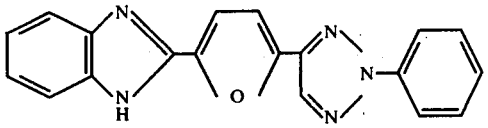

EXAMPLE 18 (interconversion process)

Following the procedure of Example 9 and using appropriate starting materials, the following compound is obtained

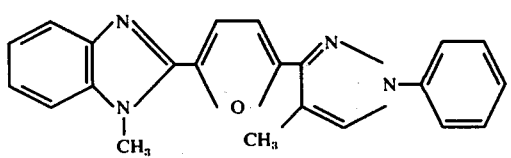

(a)

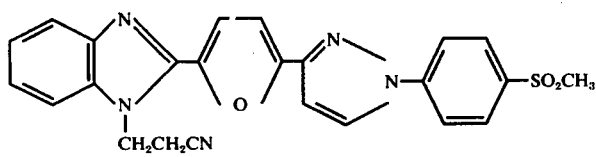

(b)

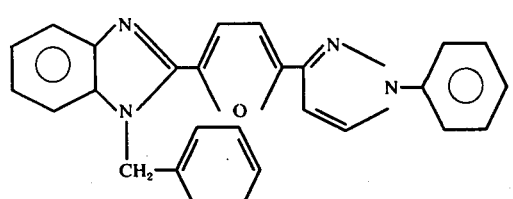

(c)

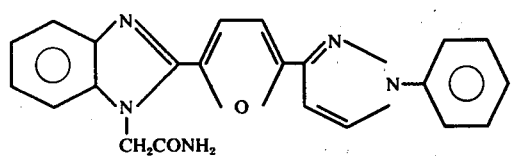

(d)

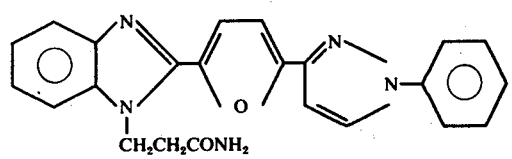

(e)

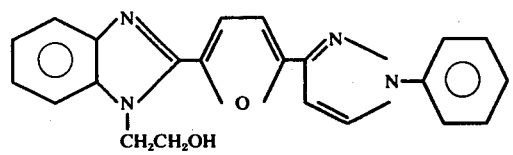

(f)

EXAMPLE 16 [process b)]

Following the procedure of Example 13 and using appropriate starting materials, the following compound is prepared

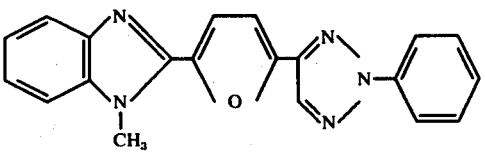

EXAMPLE 19 (quaternisation)

By quaternising the compounds of the above Examples 15a, 15b, 16, 18 and 2, following the procedure of Example 11 of our aforesaid Application, the following compounds are obtained.

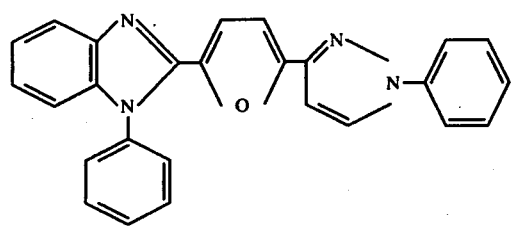

EXAMPLE 17 [process ai)]

Following the procedure of Example 10 and using appropriate starting materials, the following compound is obtained

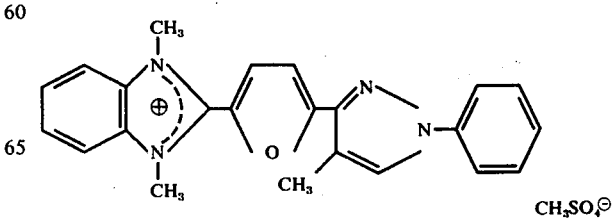

-continued

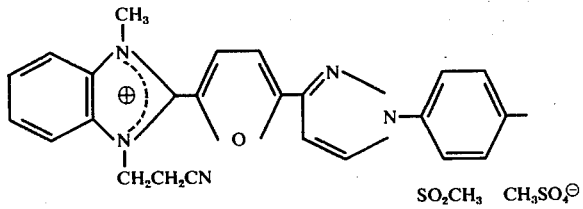

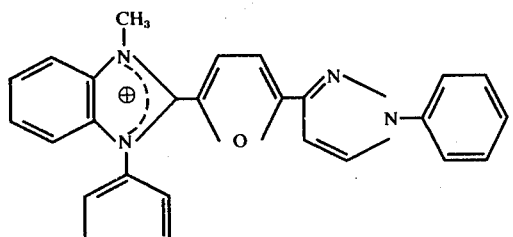

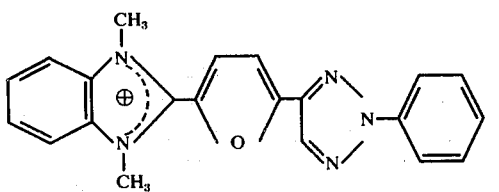

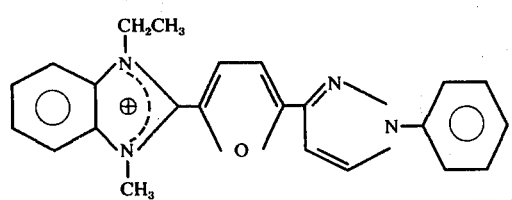

in the latter case, diethylsulphate being used in place of dimethylsulphate.

EXAMPLE 20 (quaternisation)

The pyrazole described in Example 2 was stirred with chloroacetonitrile (3.5g) in dimethylformamide (30 ml) containing sodium iodide (0.6g). The mixture was heated to 100° C and stirred at 100° C for 6 hours. Water (100 ml) was added to the mixture which was reheated to 100° C and filtered hot to remove insoluble material. The filtrate was allowed to cool to 20° C and the solid product filtered, washed with water and dried to give the quaternary salt of formula

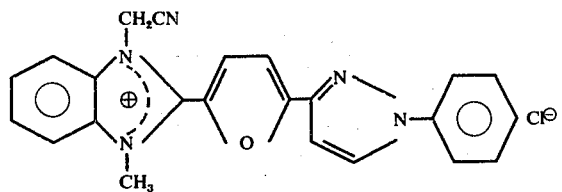

as a pale yellow solid.

EXAMPLE 21 (quaternisation)

Following the procedure of Example 20 and using the appropriate quaternising agent, the following compounds are obtained

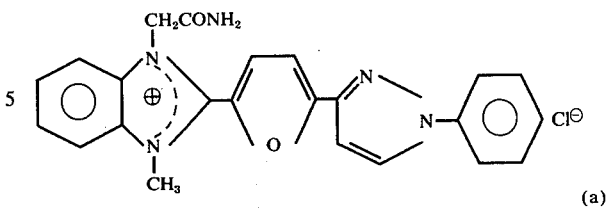

(a)

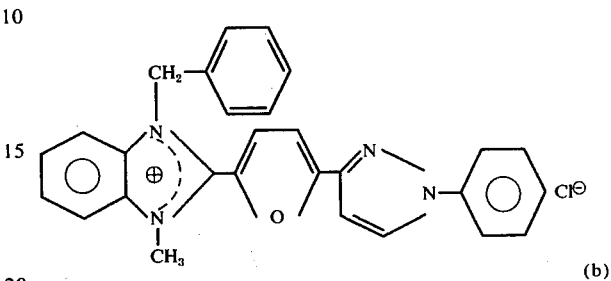

(b)

EXAMPLE 22 [process b)]

2-(2′)-(1-ethoxycarbonylmethylbenzimidazolyl)-5-(3′)-(1-phenylpyrazolinyl)-furan (10.92 g) was stirred with manganese dioxide (3.56 g) in glacial acetic acid (55 ml). The mixture was heated to the boil, stirred under reflux for 1 hour, and then filtered hot to remove excess manganese dioxide and then cooled to 20° C. The mixture was then diluted with water (100 ml) and stirred until the product solidified. The precipitate was then filtered off, washed well with water and dried to give the pyrazole of formula

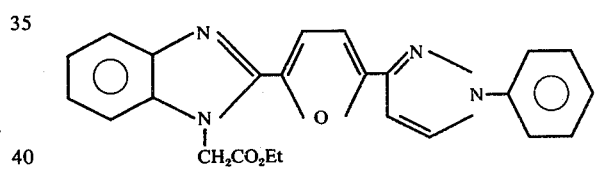

as a white solid.

The pyrazoles shown in the table were prepared in a similar way to the pyrazole of Example 1 and are of formula

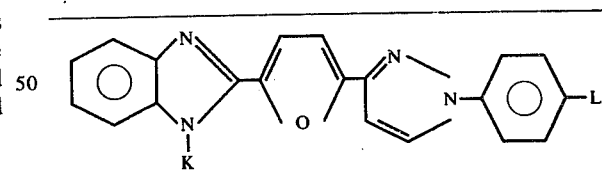

| Example | K | L | Appearance |
|---|---|---|---|
| 23 | —CH$_2$CO$_2$Et | Cl | White solid |
| 24 | —CH$_2$CO$_2$Me | H | White solid |
| 25 | —CH$_2$CON(CH$_3$)$_2$ | H | White solid |
| 26 | —CH$_2$—CH=CH$_2$ | H | White solid |
| 27 | —CH$_2$CO$_2$H | H | White solid |

EXAMPLE 28 (interconversion)

The pyrazole described in Example 22 (4g) was mixed with dimethylaminopropylamine (10 ml) and the mixture heated to the boil and stirred under reflux for 1 hour. The mixture was cooled and filtered and the solid washed with water to give the pyrazole of formula

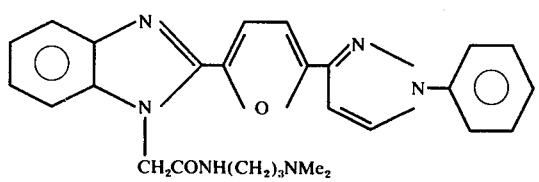

as a white solid.

EXAMPLE 29

The pyrazole of formula

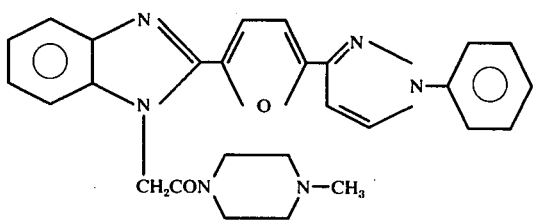

was prepared in a similar way to the pyrazole described in Example 22 using the appropriate starting materials and was obtained as a white solid.

EXAMPLE 30 (quaternisation)

The triazole described in Example 10, above, (9.8g) was stirred with ethylbromoacetate (3.6ml) and anhydrous potassium carbonate (4.1g) in acetone (100ml). The mixture was heated to the boil, and stirred under reflux for 2 hours. The reaction mixture was then cooled to 20° C, filtered and washed well with water to give the triazole of formula

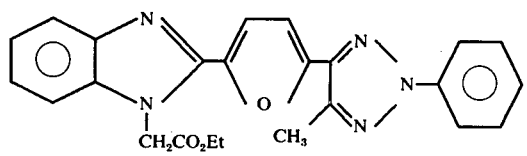

as a white solid.

EXAMPLE 31 (quaternisation)

The pyrazole described in Example 22 (8.1 g) was mixed with ethyl bromoacetate (3.7 g) in dioxan (100 ml). The mixture was heated to the boil and stirred under reflux for 20 hours. The reaction mixture was cooled and filtered and the solid washed with dioxan and dried to give the pyrazole of formula

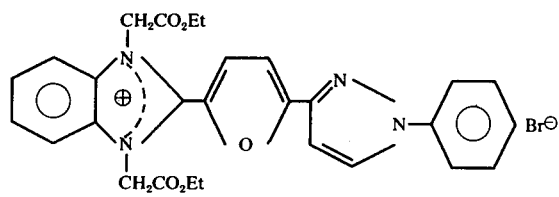

as a pale yellow solid.

The pyrazoles shown in the following table were prepared in a similar way to the pyrazole of Example 31, using appropriate starting materials.

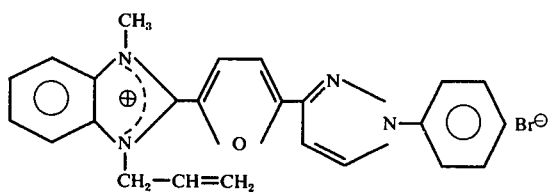

| Example | M | K | L | A |
|---|---|---|---|---|
| 32 | —CH$_2$CO$_2$Et | CH$_3$ | H | CH$_3$SO$_4$ |
| 33 | —CH$_2$CO$_2$Et | CH$_3$ | Cl | CH$_3$SO$_4$ |
| 34 | —CH$_2$CO$_2$CH$_3$ | —CH$_2$CO$_2$CH$_3$ | H | Br |
| 35 | —CH$_2$CON(CH$_2$CH$_3$)(CH$_3$) | CH$_3$ | H | CH$_3$SO$_4$ |
| 36 | —CH$_2$—CH=CH$_2$ | CH$_3$ | H | CH$_3$SO$_4$ |

EXAMPLE 37 (quaternisation)

The pyrazole described in Example 2 (13.6 g), allyl bromide (6g), sodium iodide (0.6g) and dimethylformamide (30 ml) were stirred together at 100° C for 4 hours. The dimethylformamide was evaporated off under reduced pressure leaving a solid residue which was crystallized from boiling water to give the pyrazole of formula as a pale yellow solid.

The pyrazoles shown in the following table were prepared in a similar way to the pyrazole described in Example 32 using appropriate quaternising agents.

| Example | R$_5$ | R$_4$ | R$_{11}$ | A |
|---|---|---|---|---|
| 38 | CH$_3$ | —CH$_2$CO$_2$CH$_3$ | H | Cl |
| 39 | CH$_3$ | —CH$_2$CO$_2$Et | H | Br or Cl |
| 40 | CH$_3$ | —CH$_2$CO$_2$Et | Cl | Br |
| 41 | CH$_3$ | —CH$_2$CON ME$_2$ | H | Cl |
| 42 | CH$_3$ | —CH$_2$CO$_2$H | H | Br |

EXAMPLE 43 (quaternisation)

The triazole described in Example 30 was quaternised with dimethyl sulphate in dioxan using conditions similar to those described in Example 31 to give the triazole of formula

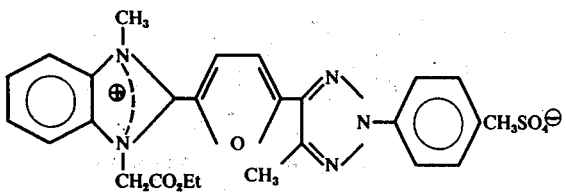

as a pale yellow solid.

APPLICATION EXAMPLE A

A 5 g piece of polyacrylonitrile ('Orlon' 75) was entered at 40° into a solution containing 10 milligrams of the pyrazole described in Example 2, 0.3 g of the condensation product of chloroacetic acid and a fatty alcohol ethylene oxide adduct and 1.5 ml of 10 % aqueous acetic acid made up to 200 ml with water. The pyrazole was added as a 0.2 % solution in 2-ethoxy ethanol. The temperature of the bath was raised to 90°–95° over 30 minutes and maintained at 90°–95° for a further 60 minutes. The fabric was rinsed well in hot, then cold demineralised water, and dried at 80°. The treated 'Orlon' 75 showed a brilliant whitening compared with the untreated fabric.

APPLICATION EXAMPLE B

A 5 g piece of polyacrylonitrile ('Orlon' 75) was treated with 200 ml of a solution containing 25 milligrams of a quaternary salt described in Example 11 and 400 milligrams of sodium chlorite at pH 3.5. The piece was entered into the bath at 40° and the temperature of the bath was raised to 95° over 30 minutes. The application was continued for a further 60 minutes at 95°. At the end of the application, the piece was taken out and antichlored in 200 mls of a solution containing 400 milligrams of sodium metabisulphite for 10 minutes. After the treatment, the piece was rinsed and dried in the oven at 80° under tension. The treated 'Orlon' 75 showed a brilliant whitening compared with the untreated fabric.

Following the procedure of Application Example B, above, but replacing the brightener used therein by the compound of Example 39, the compound of Example 3, and the compound of Example 3 quaternised using dimethylsulphate, similar results are obtained, hues of the brightened substrate being blue, blue, and neutral, respectively.

What is claimed is:

1. A compound useful as an optical brightening agent of the formula:

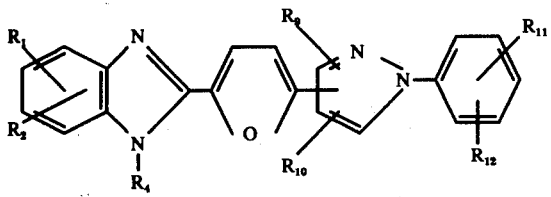

in which the 1-phenyl-pyrazolyl ring is bound at its 3- or 5-position to the furan ring and in which $R_1$ $R_2$, independently, signify hydrogen, $C_{1-4}$alkyl, $C_{1-4}$alkoxy, chlorine, fluorine or $C_{1-4}$alkoxy-carbonyl, $R_4$ signifies hydrogen; phenyl; unsubstituted $C_{1-4}$alkyl or $C_{1-4}$alkyl substituted by a substituent selected from hydroxy, cyano, amino-carbonyl, phenyl, $C_{2-4}$alkenyl, carboxy, $C_{1-4}$alkoxy-carbonyl, $C_{1-4}$alkoxy-$(C_{1-4})$-alkoxy-carbonyl, $-CONHR_{18}$ and $-CONR_{19}R_{20}$, $R_{18}$ signifies $C_{1-4}$alkyl, unsubstituted or substituted by a di-$(C_{1-4})$-alkylamino group, either $R_{19}$ and $R_{20}$, independently, have one of the significances of $R_{18}$, or are joined to form, with the nitrogen atom, a piperidino ring, either $R_9$ and $R_{10}$, independently, signify hydrogen, $C_{1-4}$alkyl or phenyl, provided both do not simultaneously signify phenyl, one of $R_9$ and $R_{10}$ signifies a 4-bromo- or 4-chlorosubstituent, the other being as defined above, $R_{11}$ and $R_{12}$, independently, signify hydrogen, $C_{1-4}$-alkyl, $C_{1-4}$alkoxy, chlorine, fluorine, cyano, $C_{1-4}$alkoxycarbonyl, $-CONR_{14}R_{15}$, $-SO_2NR_{14}R_{15}$, $-SO_2R_{16}$ or $-SO_3M$, with the proviso that $R_{11}$ and $R_{12}$ do not both simultaneously signify groups selected from cyano, $C_{1-4}$alkoxy carbonyl $-CONR_{14}R_{15}$, $-SO_2NR_{14}R_{15}$ and $-SO_2R_{16}$, either $R_{14}$ and $R_{15}$, independently, signify hydrogen, unsubstituted $C_{1-8}$alkyl, or $C_{1-4}$alkyl substituted by a substituent selected from hydroxy, cyano and aminocarbonyl, or $R_{14}$ and $R_{15}$, together with the nitrogen atom to which they are attached, signify a piperidino ring $R_{16}$ signifies $C_{1-4}$alkyl, and M signifies hydrogen or a non-chromophoric cation;

in free base, acid addition or quaternary ammonium salt form.

2. A compound according to claim 1 where $R_{14}$ and $R_{15}$, independently, signify hydrogen, unsubstituted $C_{1-8}$alkyl or $C_{1-4}$alkyl substituted by a substituent selected from hydroxy, cyano and aminocarbonyl, and $R_{19}$ and $R_{20}$, independently, have one of the significances of $R_{18}$.

3. A compound of claim 2, wherein $R_{11}$ signifies hydrogen, $C_{1-4}$alkyl, $C_{1-4}$alkoxy, chlorine, cyano, $C_{1-4}$-alkoxycarbonyl, $-SO_2R_{16}$, $-CONR_{14}R_{15}'$, $-SO_2NR_{14}R_{15}$ or $-SO_3M$, where $R_{14}$ and $R_{15}$, independently, signify hydrogen or $C_{1-4}$alkyl.

4. A compound of claim 3, wherein $R_{11}$ signifies hydrogen, $C_{1-4}$alkyl, $C_{1-4}$alkoxy, chloro, cyano, $-CONH_2$, $-SO_2NH_2$ or $-SO_2CH_3$.

5. A compound of claim 4, wherein $R_{11}$ signifies hydrogen or chloro.

6. A compound of claim 3, wherein $R_1$ and $R_2$, independently, signify hydrogen, $C_{1-4}$alkyl or $C_{1-4}$alkoxy.

7. A compound of claim 6, wherein $R_1$ and $R_2$ both signify hydrogen.

8. A compound of claim 3, wherein $R_4$ signifies hydrogen, $C_{1-4}$alkyl, cyanomethyl, β-cyanoethyl, β-hydroxyethyl, benzyl, phenyl, $C_{1-4}$alkoxycarbonyl-$C_{1-4}$alkyl, aminocarbonyl($C_{1-2}$)alkyl, dimethylamino carbonyl-($C_{1-2}$)alkyl or carboxy-($C_{1-2}$)alkyl.

9. A compound of claim 8, wherein $R_4$ signifies hydrogen, $C_{1-4}$alkyl, β-cyanoethyl, phenyl or $C_{1-4}$alkoxycarbonyl-$(C_{1-4})$-alkyl.

10. A compound of claim 9, wherein $R_4$ signifies hydrogen, methyl or $C_{1-4}$alkoxycarbonyl-$(C_{1-4})$alkyl.

11. A compound of claim 10, wherein any $C_{1-4}$-alkoxycarbonyl-$(C_{1-4})$-alkyl is methoxy- pr ethoxycarbonylmethyl.

12. A compound of claim 3, wherein $R_9$ and $R_{10}$, independently, signify hydrogen or $C_{1-4}$alkyl, or one of $R_9$ and $R_{10}$ signifies a 4-chloro substituent, the other hydrogen or $C_{1-4}$alkyl.

13. A compound of claim 12, wherein $R_9$ and $R_{10}$ both signify hydrogen.

14. A compound of claim 3, wherein $R_{12}$ is hydrogen.

15. A compound of claim 1, wherein $R_4$ is hydrogen, phenyl, unsubstituted $C_{1-4}$alkyl or $C_{1-4}$alkyl substituted by a substituent selected from hydroxy, cyano, aminocarbonyl and phenyl.

16. A compound of claim 3 wherein $R_9$ and $R_{10}$, independently, signify hydrogen or $C_{1-4}$alkyl and $R_{12}$ signifies hydrogen.

17. A compound of claim 16, of the formula

[structural formula]

in free base, acid addition or quaternary ammonium salt form.

18. A compound of claim 17 of the formula

[structural formula]

in which $R_{11}$ is hydrogen, $C_{1-4}$alkyl, $C_{1-4}$alkoxy, chloro, cyano, $-CONH_2$, $-SO_2NH_2$ or $SO_2CH_3$.

19. A compound of claim 16 wherein $R_1$ and $R_2$ are hydrogen and $R_4$ is hydrogen, $C_{1-4}$alkyl or $C_{1-4}$alkyl substituted by a $C_{1-4}$alkoxycarbonyl, in free base, acid addition or quaternary ammonium salt form.

20. A compound of claim 18 in which $R_1$ and $R_2$ are hydrogen.

21. A compound of claim 19, wherein $R_4$ is hydrogen, methyl, ethoxycarbonylmethyl or methoxycarbonylmethyl.

22. A compound of claim 21, wherein $R_4$ is methyl, ethoxycarbonylmethyl or methoxycarbonylmethyl. phenyl, unsubstituted $C_{1-4}$alkyl or $C_{1-4}$alkyl substituted by a substituent selected from hydroxy, cyano, aminocarbonyl and phenyl.

23. A compound of claim 22, of formula

[structural formula]

in free base, acid addition salt or quaternary ammonium salt form.

24. A compound of claim 23, in free base or acid addition salt form.

25. A compound of claim 22 of the formula

[structural formula]

26. A compound of claim 23, of formula

[structural formula]

27. A compound of claim 22, of formula in free base, acid addition or quaternary ammonium salt form.

[structural formula]

28. A compound of claim 27, in free base or acid addition salt form.

29. A compound of claim 27, of formula

[structural formula]

30. A compound useful as an optical brightener, of formula

[structural formula]

where $An^\ominus$ is $Cl^\ominus$ or $Br^\ominus$.

* * * * *